United States Patent [19]

Bergeron, Jr.

[11] Patent Number: 5,364,965
[45] Date of Patent: Nov. 15, 1994

[54] ANALOGS OF DESFERRIOXAMINE B AND METHOD FOR SYNTHESIS THEREOF

[75] Inventor: Raymond J. Bergeron, Jr., Gainesville, Fla.

[73] Assignee: University of Florida, Gainesville, Fla.

[21] Appl. No.: 114,166

[22] Filed: Sep. 1, 1993

Related U.S. Application Data

[62] Division of Ser. No. 987,754, Dec. 9, 1992.

[51] Int. Cl.$^5$ ............................................ C07C 259/06
[52] U.S. Cl. .................................................... 562/623
[58] Field of Search ......................................... 562/623

[56] References Cited

U.S. PATENT DOCUMENTS 4,987,253  1/1991  Bergeron ............................. 562/623

OTHER PUBLICATIONS

Bergeron et al, "An Efficient Total Synthesis of Desferrioxamine B," *Journal of Organic Chemistry*, vol. 53, pp. 3131–3134 (1988).

Bickel et al, "Metabolic Products of Actinomycetes. Isolation and Synthesis of 1-amino-5-hydroxylamino--pentane, and Essential Hydrolysis Product of Ferrioxamine and Ferrimycin," *Helv. Chim. Acta.*, vol. 43, pp. 901–904 (1960).

Prelog et al, "Metabolic Products of Actinomycetes. Synthesis of Ferrioxamine B and D$_1$," *Helv. Chim. Acta.*, vol. 45, pp. 631–637 (1962).

*Primary Examiner*—José G. Dees
*Assistant Examiner*—Joseph M. Conrad
*Attorney, Agent, or Firm*—Kerkam, Stowell, Kondracki & Clarke

[57] ABSTRACT

The invention relates to novel analogs of desferrioxamine, homologs thereof and methods for their synthesis.

4 Claims, 9 Drawing Sheets

FIG. 1[A]
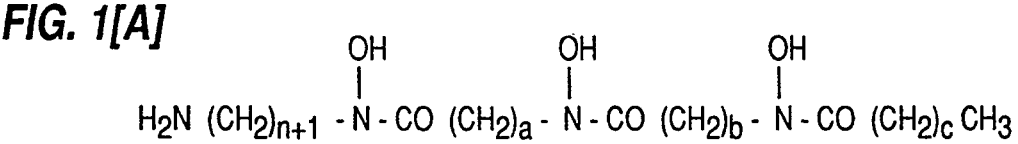
FIG. 1[B]
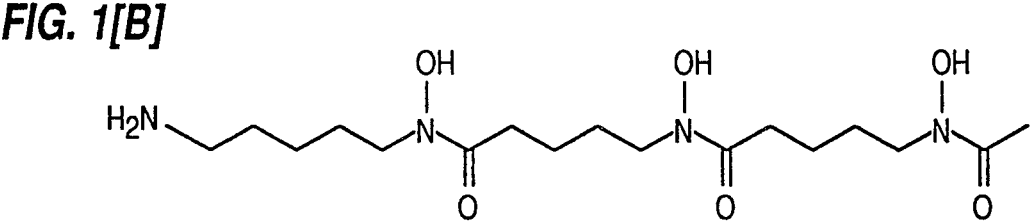
FIG. 1[C]
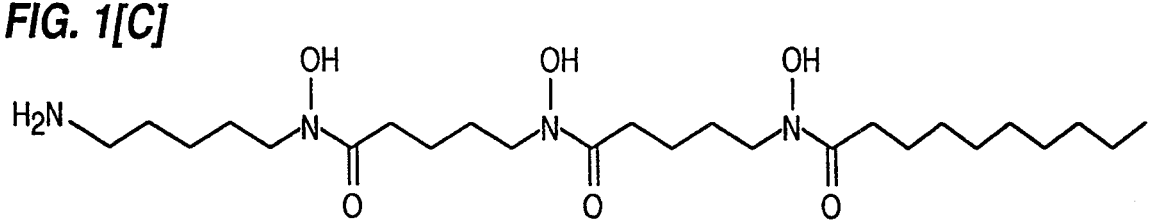
FIG. 1[D]
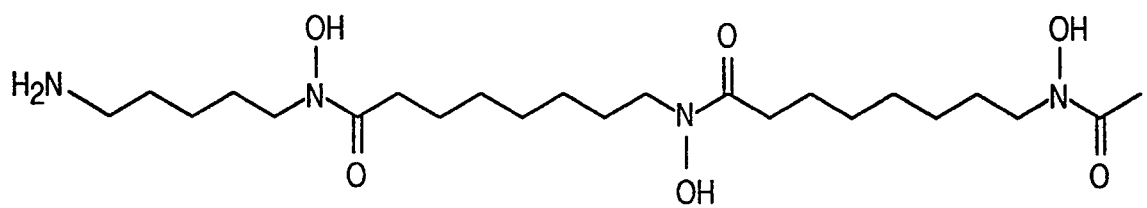

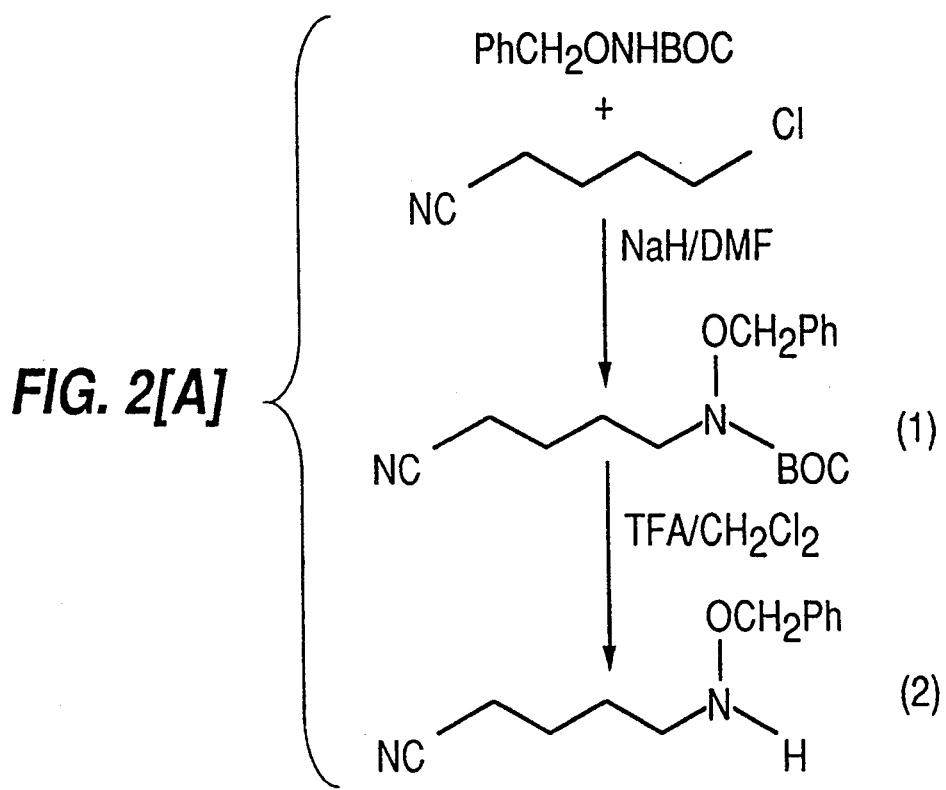
FIG. 2[A]

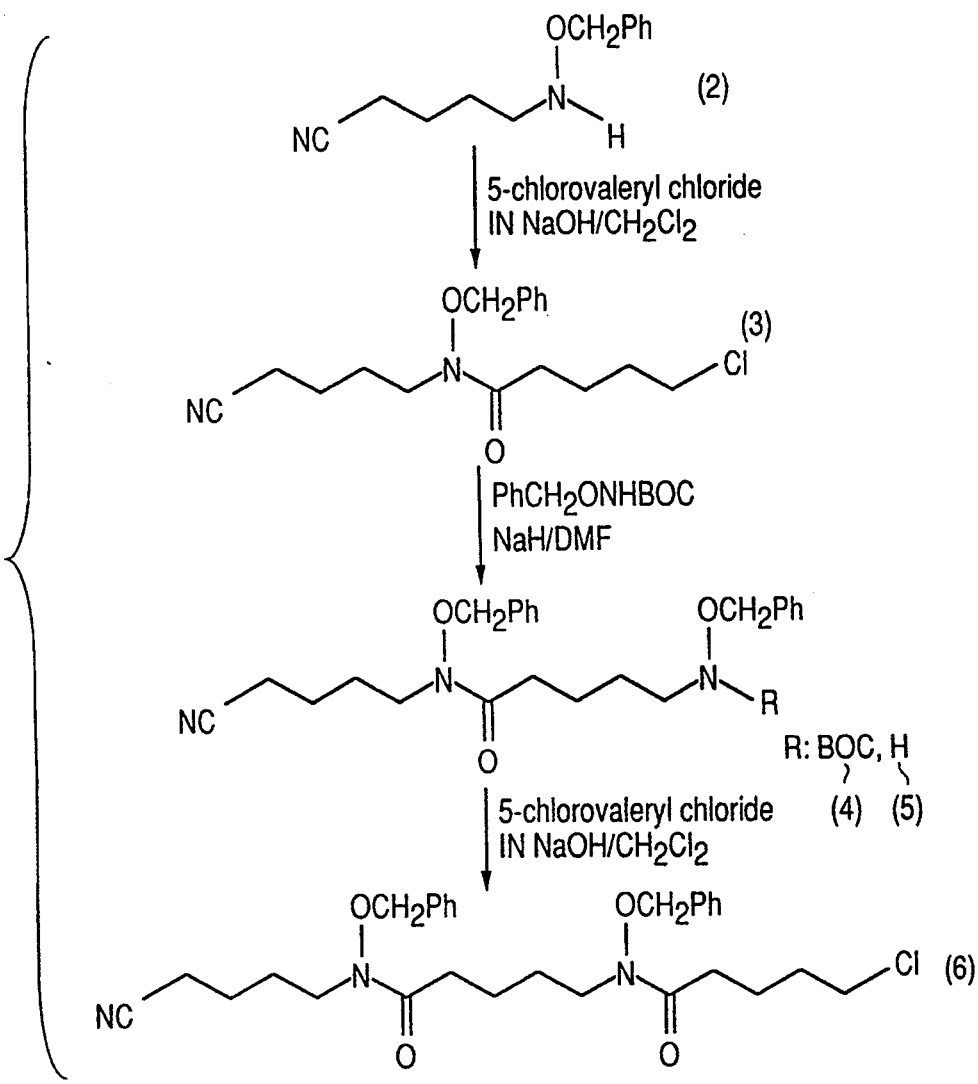
FIG. 2[B]

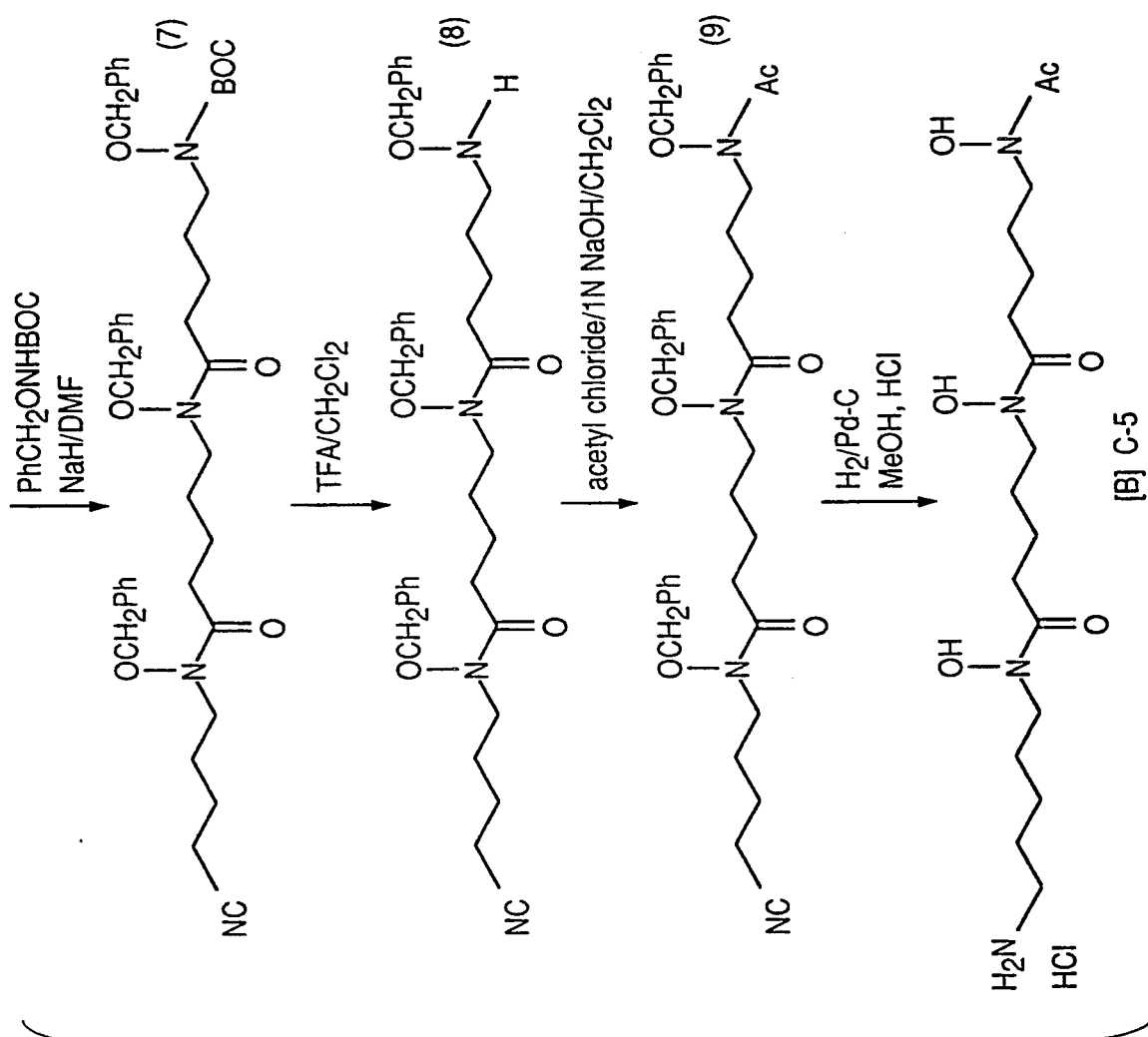
FIG. 2[C]

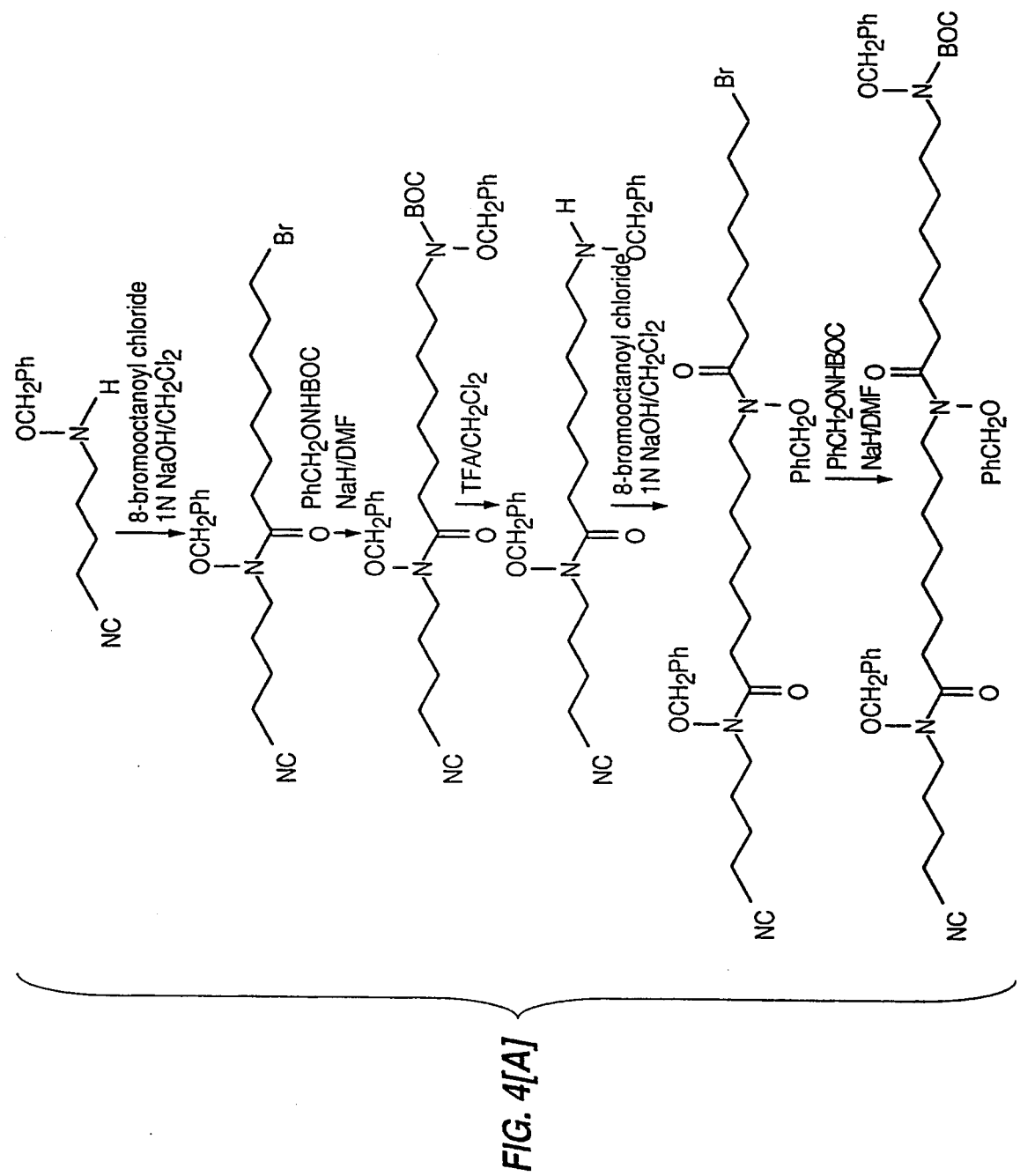
FIG. 4[A]

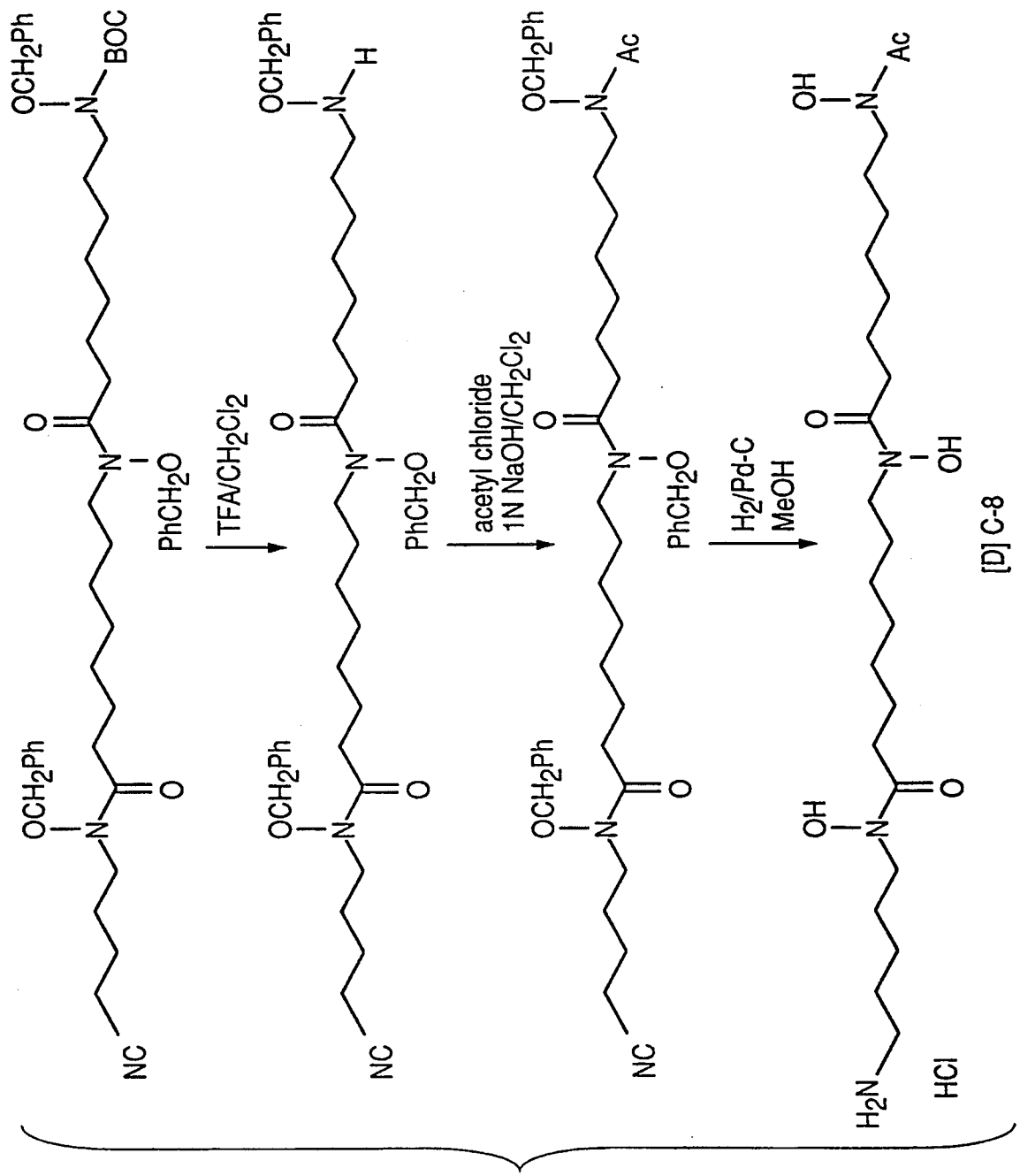
FIG. 4[B]

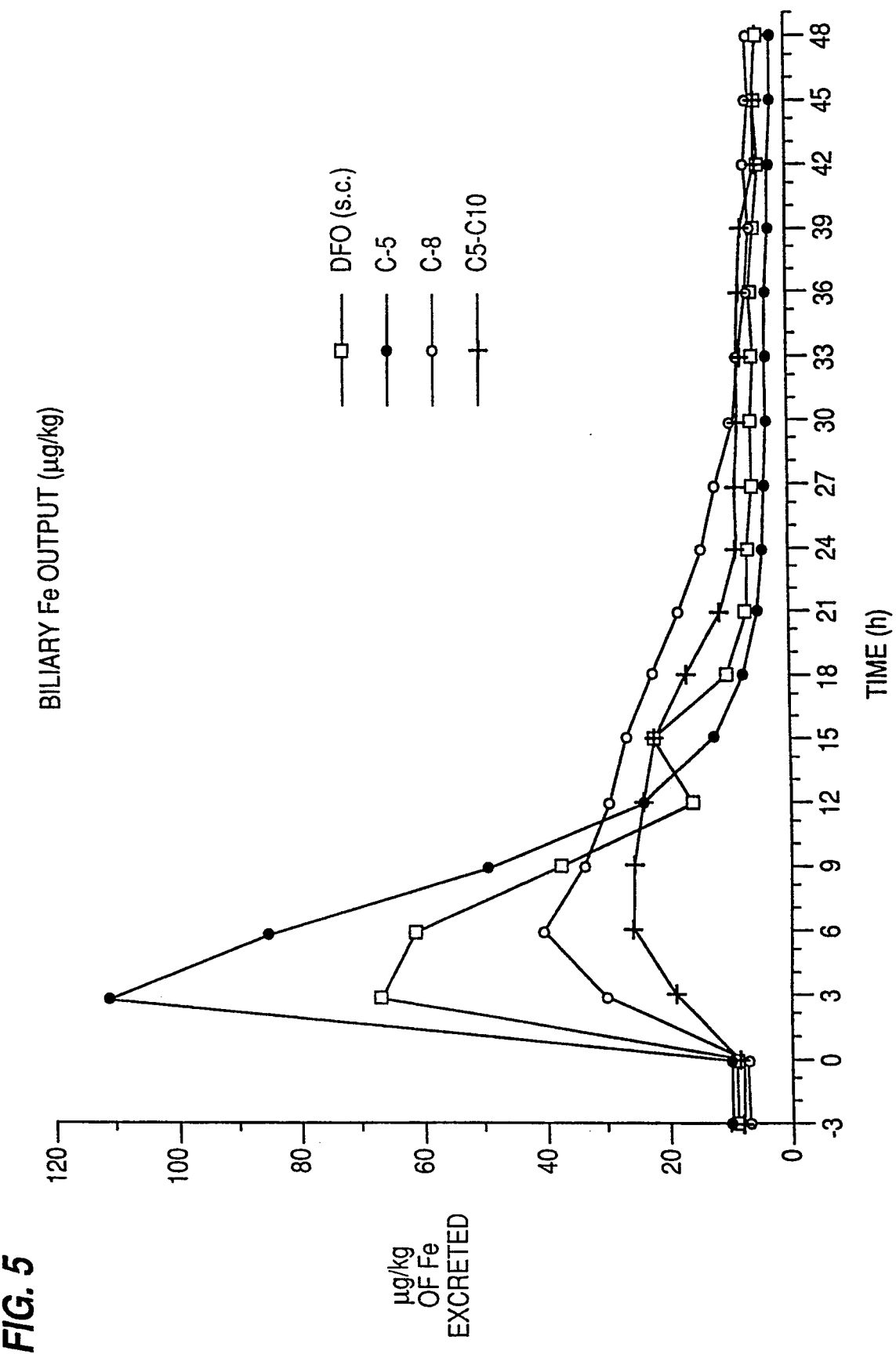

ANALOGS OF DESFERRIOXAMINE B AND METHOD FOR SYNTHESIS THEREOF

RELATED APPLICATIONS

This is a division of application Ser. No. 07/987,754 filed Dec. 9, 1992.

This application contains subject matter related to that described and claimed in U.S. Pat. No. 4,987,253, as well as U.S. patent application Ser. No. 07/784,949 filed Oct. 30, 1991, the entire contents of both of which are incorporated herein by reference.

Support for the research which led to the present invention was provided by the National Institutes of Health (NIH) Grant No. 5R01-HL-42817.

BACKGROUND OF THE INVENTION

1. Field of the Invention

The present invention relates to an improved method for the synthesis of analogs of desferrioxamine B and homologs thereof.

2. Description of the Prior Art

The microbial iron chelator, siderophore, desferrioxamine B [N'-[5-[4-[[5-acetylhydroxyamino)pentyl]amino-1,4-dioxobutyl]hydroxyamino]pentyl]-N-(5-aminopentyl)-N-hydroxybutane diamide] was isolated from *Streptomyces pilosus* and characterized by Bickel ["Metabolic products of actinomycetes. Ferrioxamine B," *Helv. Chim. Acta.*, Vol. 43, pp. 2129-2138] in 1960. It is a linear trihydroxamate ligand which forms a very stable hexacoordinate, octahedral [Modell et al, "The Clinical Approach to Thalassaemia," Grune and Stratton, London, pp. 217-241 (1984)] complex with Fe (III), $K_f = 1 \times 10^{30} M^{-1}$. The ligand employs its three bidentate hydroxamate units in chelating metal ions.

Although desferrioxamine B will bind a number of different +3 cations, e.g., Al (III), Ga (III), Cr (III), it exhibits a high specificity for Fe (III), and is utilized by *Streptomyces pilosus* for the acquisition of iron from the environment. Because of the metal selectivity and low toxicity of the ligand, it has been employed in the treatment of several iron overload diseases, e.g., thalassaemia ["Development of Iron Chelators for Clinical Use," Martell et al, eds., Elsevier, North Holland; N.Y. (1981)]. However, desferrioxamine B does not offer a completely satisfactory solution to the iron overload problem. The drug is cleared by the kidneys and has a very short half-life in the body; thus, the patient must be maintained on constant infusion therapy. It is not orally effective. Because of these shortcomings, investigators have explored the potential of other ligands as therapeutic iron chelators. To date, these investigations have not included modification of the desferrioxamine molecule simply because of the lack of high yield of facile approaches to the synthesis of the molecule.

Desferrioxamine B was first synthesized in 1962 by Prelog et al ["Metabolic products of actinomycetes. Synthesis of Ferrioxamines B and D," *Helv. Chim. Acta.*, Vol 45, pp. 631-637 (1962)]. However, because of the number of steps in the synthesis and the low yield of the sequence, the method does not enable the production of large quantities of the chelator or its analogs. A retro-synthetic analysis of the ligand reveals that the desferrioxamine molecule is made up of two fundamental units: 1-amino-5-(N-hydroxyamino)pentane and succinic acid. The key to its synthesis is the production of this amino-hydroxyaminopentane unit and its condensation with succinic acid. Prelog approached this problem beginning with the starting material 1-amino-5-nitropentane, an amine which was accessible in only 46% yield [Bickel et al, "Metabolic products of actinomycetes. Isolation and synthesis of 1-amino-5-(hydroxyamino)pentane, an essential hydrolysis product of ferrioxamine and ferrimycin," *Helv. Chim, Acta.*, Vol. 43, pp. 901-904 (1960)]. This compound was next N-carbobenzoxylated and the terminal nitro group reduced to the corresponding hydroxyamino group. This key intermediate was condensed with succinic acid followed by a series of other dicyclohexylcarbodiimide catalyzed acylations along with several reductions to produce desferrioxamine B. The overall yield of this eleven-step sequence was 6%.

Although desferrioxamine is currently the drug of choice in the treatment of thalassemia, it nevertheless suffers from several shortcomings. The drug is not orally effective and, therefore, must be administered by infusion. Furthermore, because of its short half-life in the body, patients must be maintained on continuous infusion therapy for extended periods of time. As a result, patient compliance is the principal difficulty associated with the drug. In order to overcome these problems, investigators have explored the therapeutic potential of alternative iron chelators over the years, albeit with somewhat limited success. It was an object of the search that led to the present invention to identify the minimal structural requirements of the desferrioxamine platform which are still compatible with the molecule's iron-clearing properties. Once having identified such a pharmacophore, it was converted to pharmacophores which are more readily absorbed in the gastrointestinal tract, specifically, hexacoordinate DFO analogs in which the amides are removed and the molecules are shortened.

Bergeron et al ["An Efficient Total Synthesis of Desferrioxamine B," *J. Org. Chem.*, vol 53, pp 3131-3134 (1988)] reported a total synthesis of desferrioxamine B (DFO) in which the construction moved from the N-acetyl to the primary amine end of the molecule.

U.S. Pat. No. 4,987,253 and U.S. patent application Ser. No. 07/784,949 filed Oct. 30, 1991, each disclose novel syntheses for desferrioxamine B and analogs and homologs thereof.

It is an object of the present invention to provide novel, improved, high yield methods for the production of analogs of desferrioxamine B and homologs thereof.

SUMMARY OF THE INVENTION

The above and other objects are realized by the present invention, one embodiment of which comprises a method for synthesizing analogs of desferrioxamine B or a homolog thereof having the formula:

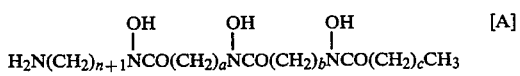

$$\begin{array}{ccc} OH & OH & OH \\ | & | & | \end{array} \quad [A]$$
$$H_2N(CH_2)_{n+1}NCO(CH_2)_aNCO(CH_2)_bNCO(CH_2)_cCH_3$$

wherein:

each n may be the same or different and is an integer from 1 to 10;

a and b may be the same or different and are integers from 1 to 10; and c may be an integer from 0 to 10;

comprising:

(a) cleaving Q from a compound having the formula:

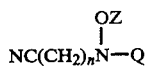   (1)

wherein Z is a hydroxyl protecting group and Q is an amino protecting group, to produce a protected hydroxylamine having the formula:

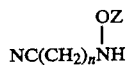   (2)

(b) condensing hydroxylamine (2) with a carboxylic acid halide having the formula:

$XOC(CH_2)_aX$ or the corresponding anhydride, wherein a is an integer from 1 to 10 to produce a compound having the formula:

   (3)

wherein X is a reactive halide, (c) alkylating a compound having the formula Z—ONH—Q with compound (3) to produce a compound of the formula:

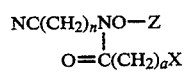   (4)

(d) cleaving Q from compound (4) to produce a compound having the formula:

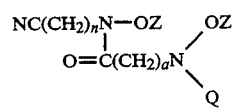   (5)

(e) acylating compound (5) with a halo-substituted carboxylic acid halide having the formula:

$XOC(CH_2)_bX$ or the corresponding anhydride, wherein b is an integer from 1 to 10 and X is as defined above to produce a compound having the formula:

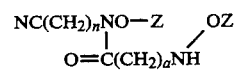   (6)

(f) acylating a compound having the formula Z—ONH—Q with compound (6) to produce a compound having the formula:

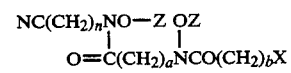   (7)

(g) cleaving Q from compound (7) to produce the amine:

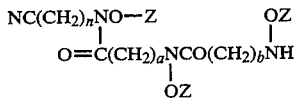   (8)

(h) acylating compound (8) with an acyl halide having the formula $XOC(CH_2)_cCH_3$ or the corresponding anhydride to produce a compound having the formula:

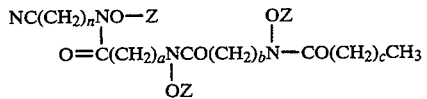   (9)

(i) reducing compound (9) to produce a compound of formula [A]:

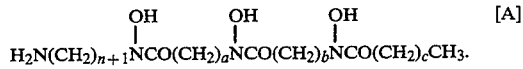   [A]

$H_2N(CH_2)_{n+1}NCO(CH_2)_aNCO(CH_2)_bNCO(CH_2)_cCH_3$.

Further embodiments of the invention comprise the compounds of formula [A] described above.

BRIEF DESCRIPTION OF THE DRAWINGS

FIGS. 1A–1D depicts the structural formulae of the DFO analogs of the present invention.

FIGS. 2A–2C, 3 and 4A–4B depict reaction schemes for methods of the invention for producing the DFO analogs depicted in FIG. 1.

FIG. 5 is a graphical depiction of the cumulative biliary iron clearance induced by analogs of the invention compared with that of DFO when administered subcutaneously.

DETAILED DESCRIPTION OF THE INVENTION

Figure 3:
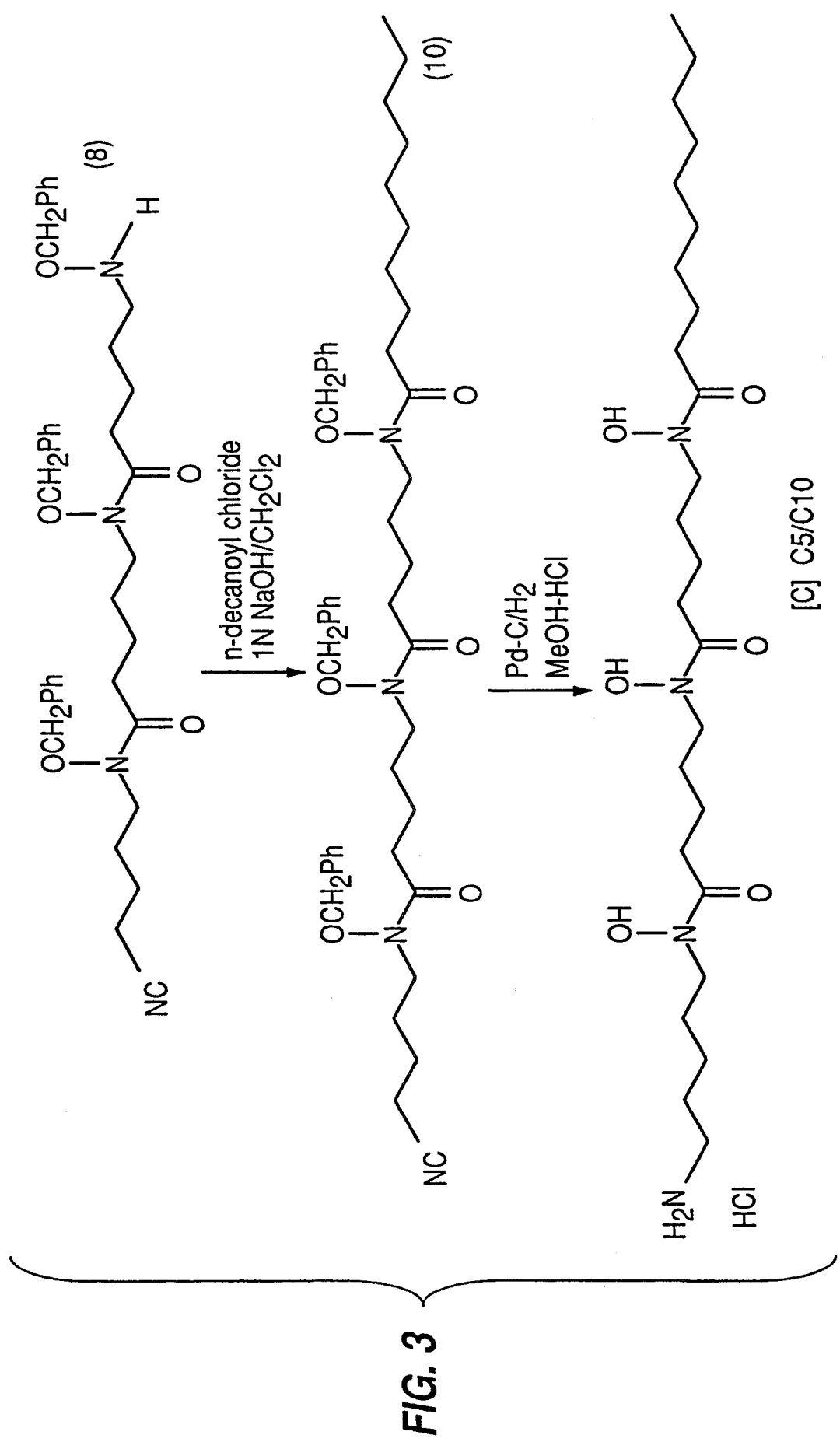
Figure 6:
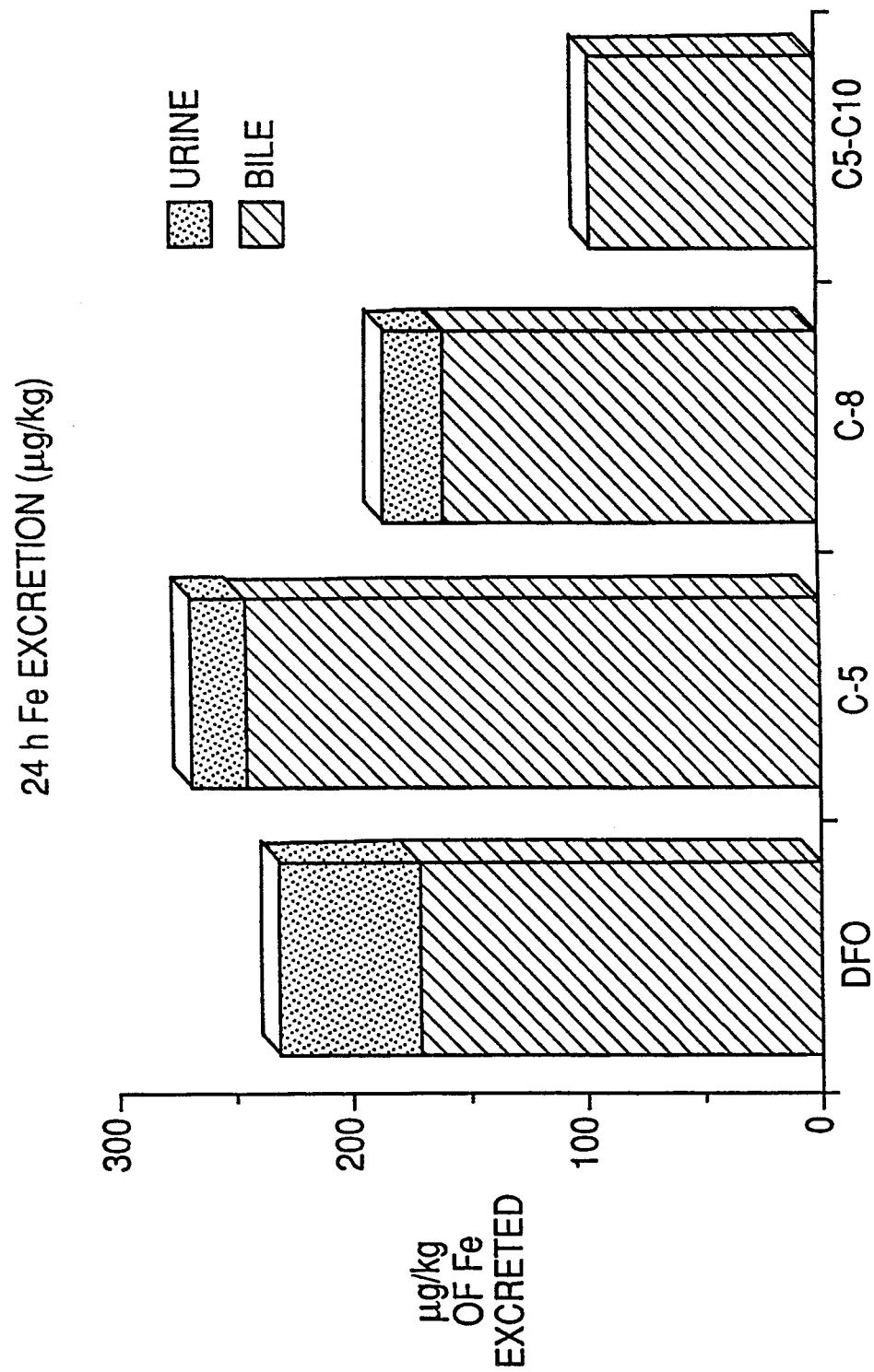
FIG. 6 is a graphical depiction of the ferrokinetic clearance properties of the analogs of the invention compared with that of DFO when administered subcutaneously.

Microorganisms produce a group of low molecular weight chelators, siderophores [Bergeron, "Synthesis and Solution Structures of Microbial Siderophores," *Chem. Rev.*, Vol. 84, pp. 587–602 (1984); Tait, "The Identification and Biosynthesis of Siderochromes Formed by *Micrococcus denitrificans*, *Biochem. J.*, vol. 146, pp. 191–204 (1975); Griffiths et al, "Vibriobactin, a Siderophore from *Vibrio cholerae*," *J. Biol. Chem.*, Vol. 259, pp. 383–385 (1984); Aksoy et al, "Hypertransfusion and Iron Chelation in Thalassaemia," p. 80, Hans Huber Publishers, Berne (1985); and Bickel et al, "Metabolic products of actinomycetes. Ferrioxamine B," *Helv. Chim. Acta.*, Vol. 43, pp. 2129–2138 (1960)] for the purpose of acquiring iron. The metal exists in the biosphere largely in the insoluble ferric state and would be otherwise inaccessible to bacteria without such ligands. Although a large number of siderophores have been identified, they fall largely into two structural classes: the catecholamides and the hydroxamates [Bergeron, supra]. Many of the ligands of both structural types contain polyamine backbones. While the hexacoordinate catecholamides parabactin [Tait, supra] and vibriobactin [Griffiths et al, Supra] are predicated on the substituted triamines spermidine and norspermidine, respectively, the hydroxamates are frequently derived from the diamines, putrescine or cadaverine, or from their biochemical precursors, ornithine or lysine [Bergeron, supra]. For example, the siderophores isolated from *Streptomyces pilosus*, desferrioxamines A-I, consist of a group of hydroxamates with either repeating putrescine or cadaverine units in their backbones [Aksoy et al, supra]. The most well known of these chelators, desferrioxamine B (DFO) [Bickel et al, supra], is a linear trihydroxamate ligand which forms a very stable hexacoordinate, octahedral complex [Modell et al, "The Clinical Approach to Thalassaemia," p. 217, "Grune and Stratton, London (1984)] with iron (III), $K_f = 1 \times 10^{30} M^{-1}$. Although DFO binds a number of different +3 cations, e.g., Al (III), Ga (III), Cr (III), it exhibits a high specificity for iron (III). It is not too surprising then that the mesylate salt of desferrioxamine, Desferal, has been employed in the treatment of several iron overload diseases such as thalassemia [Anderson, "Inorganic Chemistry in Biology and Medicine," Chapter 15, American Chemical Society, Washington, D.C. (1973); and Fisher et al, "Development of an Intravenous Desferrioxamine Mesylate Treatment Protocol for Swine: Monitoring of Desferrioxamine and Metabolites By High-Performance Liquid Chromatography," *Pharmacology*, Vol 41, pp. 263-271 (1990)]. However, the fact that patients must be continuously infused because of the short half-life of the drug in the body has compelled investigators to continue the search for better therapeutic iron chelators.

The present invention provides new analogs of DFO which are therapeutically as effective as DFO, but which have molecular weights approximately one-third less than that of DFO. Moreover, the invention identifies the platform or core structure required for compounds having DFO's therapeutic characteristics.

The total synthesis (see FIG. 2) of the C-5 amide-less DFO analog [B] begins with the generation and selective deprotection of triprotected N-hydroxycadaverine (1). In this versatile reagent, the primary amine is masked as a nitrile, while the hydroxylamine is N-tert-butoxycarbonyl, O-benzyl diprotected. The hydroxylamine oxygen in (1) remains protected by the benzyl moiety until catalytic ($H_2$/Pd-C) unmasking of the hydroxamic acid chelator in the last step of the total synthesis. The synthesis of reagent (1) starts with the conversion of O-benzylhydroxylamine hydrochloride to its crystalline N-(tert-butoxycarbonyl) derivative, which was alkylated with 5-chlorovaleronitrile (NaH, DMF, NaI). Brief exposure of N-(tert-butoxycarbonyl)nitrile (1) to trifluoroacetic acid (TFA) resulted in O-benzyl-N-(4-cyanobutyl)hydroxylamine (2), thus freeing up the hydroxylamine nitrogen. Benzyloxyamine (2) was N-acylated with 5-chlorovaleryl chloride in $CH_2Cl_2$/aqueous NaOH, giving chloride (3). N-(tert-butoxycarbonyl)-O-benzylhydroxylamine was N-alkylated with (3) (NaH/DMF) to provide nitrile (4). Treatment of (4) with TFA/$CH_2Cl_2$ generated benzyloxyamine (5) which, upon acylation with 5-chlorovaleryl chloride, gave bis-hydroxamate ester (6). N-tert-butoxycarbonyl-O-benzylhydroxylamine was N-alkylated with (6) (NaH/DMF), generating (7), a hexacoordinate equivalent. Acid promoted de-tert-butoxycarbonylation of (7) to amine (8) was followed by acetylation with AcCl in aqueous NaOH to give masked amideless DFO (9). Hydrogenation of (9) under mild conditions (10% Pd-C) resulted in simultaneous debenzylation and nitrile reduction, producing C-5 amideless DFO [B].

Amine (8) can be reacted with any electrophilic reagent that one chooses (see FIG. 3). A more lipophilic C-5/C-10 amideless DFO [C] was synthesized by acylating (8) with decanoyl chloride, followed by hydrogenation of (10) as before to produce the compound [C].

The synthesis of a longer, more lipophilic (C-8) amideless DFO [D] further illustrates the flexibility of this route (see FIG. 4). Specifically, acylation of the corresponding benzyloxyamine intermediates with 8-bromooctanoyl chloride in place of 5-chlorovaleryl chloride, employing the same methodology, gives analog [D].

EXAMPLES

N-(Benzyloxy)-N-(4-cyanobutyl)-5-chloropentanamide (3)

A solution of 5-chlorovaleryl chloride (3.66 g, 23.6 mmol) in $CH_2Cl_2$ (50 mL) was slowly dripped into a mixture of amine 2 (n=4) (4.08 g, 20.0 mmol) in $CH_2Cl_2$ (100 mL) and 1N NaOH (200 mL) which had been cooled to 0° C. The mixture was stirred at 0° C. for 30 minutes and at room temperature overnight. The layers were separated and the aqueous layer was further extracted with $CH_2Cl_2$ (2×150 mL). The combined organic extracts were washed with saturated sodium chloride, and solvent was removed in vacuo. The crude oil was passed through a short silica gel column, eluting with EtOAc, to give 6.0 g (93%) of (3) as an oil; NMR δ 1.57-1.97 (m, 8H), 2.35 (t, 2H, J=6), 2.40 (t, 2H, J=6), 3.50 (t, 2H, J=6), 3.67 (t, 2H, J=6), 4.80 (s, 2H), 7.37 (s, 5H). Anal. ($C_{17}H_{23}ClN_2O_2$) C, H, N.

12-(tert-Butoxycarbonyl)-6,12-bis(benzyloxy)-7-oxo-6,12-diazadodecanenitrile (4)

N-(tert-Butoxycarbonyl)-O-benzylhydroxylamine (4.2 g, 18.8 mmol) was dissolved in DMF (120 mL) and cooled to 0° C. Sodium hydride (80%, 0.564 g, 18.8 mmol) was added, and the mixture was stirred at 0° C. for 30 minutes. A solution of (3) (6.0 g, 18.6 mmol) in DMF (30 mL) was slowly added to the cold solution which was then allowed to stir at room temperature for 20 minutes and at 80° C. overnight. The DMF was removed under high vacuum, and the reside was quenched with $H_2O$ (50 mL) and extracted with $CH_2Cl_2$ (3×70 mL). Organic extracts were washed with saturated sodium chloride, and the solvent was removed by rotary evaporation. Silica gel column chromatography, eluting with 2:1 hexane/EtOAc produced 7.29 g (77%) of (4) as an oil: NMR δ 1.50 (s, 9H), 1.40-1.90 (m, 8H), 2.30 (t, 2H, J=6), 2.40 (t, 2H, J=6), 3.40 (t, 2H, J=6), 3.63 (t, 2H, J=6), 4.77 (s, 2H), 4.80 (s, 2H), 7.33 (s, 10H). Anal. ($C_{29}H_{39}N_3O_5$), C, H, N.

6,12-Bis(benzyloxy)-7-oxo-6,12-diazadodecanenitrile (5)

Trifluoroacetic acid (25 mL) was slowly dripped into a solution of (4) (7.10 g, 13.93 mmol) in $CH_2Cl_2$ (150 mL) which had been cooled to 0° C. The solution was stirred at 0° C. for 30 minutes and at room temperature for 15 minutes. Solvent and excess TFA were removed by rotary evaporation, and the concentrate was cooled to 0° C., treated with saturated $NaHCO_3$ (150 mL) and extracted with $CH_2Cl_2$ (4×80 mL). After solvent removal, the crude oil was purified by silica gel column chromatography with 1:1 hexane/EtOAc as the eluant, generating 4.6 g (81%) of (5) as an oil: NMR δ 1.40–190 (m, 8H), 2.30 (t, 2H, J=6), 2.40 (t, 2H, J=6), 2.90 (t, 2H, J=6), 3.63 (t, 2H, J=6), 4.63 (s, 2H), 4.75 (s, 2H), 4.93 (br s, 1H), 7.27 (s, 5H), 7.33 (s, 5H). Anal. ($C_{24}H_{31}N_3O_3$) C, H, N.

17-Chloro-6,12-bis(benzyloxy)-7,13-dioxo-6,12-diazaheptadecanenitrile (6)

Compound (5) (2.44 g, 5.96 mmol) was reacted with 5-chlorovaleryl chloride (1.13 g, 7.29 mmol) in $CH_2Cl_2$ (150 mL) and 1N NaOH (200 mL) by the procedure used for (3). Silica gel column chromatography, eluting with 3% EtOH/$CHCl_3$, gave (6) in quantitative yield as an oil: NMR δ 1.50–1.87 (m, 12H), 2.23–2.53 (m, 6H), 3.47 (t, 2H, J=6), 3.60 (t, 4H, J=6), 4.77 (s, 4H), 7.33 (s, 10H). Anal. ($C_{29}H_{38}ClN_3O_4$) C, H, N.

18-(tert-Butoxycarbonyl)-6,12,18-tris(benzyloxy)-dioxo-6,12,18-triazaoctadecanenitrile (7)

N-(tert-Butoxycarbonyl)-O-benzylhydroxylamine (1.43 g, 6.40 mmol) was alkylated with (6) (3.00 g, 5.68 mmol) using NaH (80%, 0.19 g, 6.33 mmol) in DMF (100 mL), following the procedure used for (4). Column chromatography on silica gel with 4:1 hexane/EtOAc yielded 3.0 g (74%) of (7) as an oil: NMR δ 1.50 (s, 9H), 1.40–1.85 (m, 12H), 2.20–2.50 (m, 6H), 3.27–3.70 (m, 6H), 4.75 (s, 6H), 7.33 (s, 15H). Anal. ($C_{41}H_{54}N_4O_7$) C, H, N.

6,12,18-Tris(benzyloxy)-7,13-dioxo-6,12,18-triazaoctadecanenitrile (8)

Compound (7) (2.85 g, 3.99 mmol) in $CH_2Cl_2$ was treated with excess TFA following the procedure used for (5). Silica gel column chromatography, eluting with 3:2 EtOAc/hexane gave 1.4 g (57%) of (8) as an oil: NMR δ 1.43–1.83 (m, 12H), 2.20–2.50 (m, 6H), 2.90 (t, 2H, J=6), 3.60 (t, 4H, J=6), 4.63 (s, 2H), 4.75 (s, 4H), 7.28 (s, 5H), 7.33 (s, 10H). Anal. ($C_{36}H_{46}N_4O_5$) C, H, N.

6,12,18-Tris(benzyloxy)-7,13,19-trioxo-6,12,18-triazaeicosanenitrile (9)

Acetic anhydride (8 mL) was slowly added to a solution of (8) (1.25 g, 2.03 mmol) in pyridine (50 mL) and $CH_2Cl_2$ (30 mL) which had been cooled to 0° C. Stirring was continued at 0° C. for 30 minutes and then at room temperature overnight. Solvents were removed under high vacuum, and the residue was dissolved in $CHCl_3$ (120 mL), followed by washing with 0.5N HCl (2×40 mL) and saturated $NaHCO_3$ (2×40 mL). After solvent removal, the crude oil was purified by silica gel column chromatography, eluting with 3:1 EtOAc/hexane, to furnish 0.8 g (60%) of (9) as an oil: NMR δ 1.40–1.80 (m, 12H), 2.05 (s, 3H), 2.20–2.50 (m, 6H), 3.40–3.73 (m, 6H), 4.75 (s, 6H), 7.32 (s, 15H). Anal. ($C_{38}H_{48}N_4O_6$) C, H, N.

6,12,18-Trihydroxy-7,13,19-trioxo-6,12,18-triazaeicosanamine hydrochloride [A]

Compound (9) (1.000 g, 1,522 mmol) was dissolved in $CH_3OH$ (210 mL), followed by addition of 0.1N HCl (from concentrated HCl and methanol, 16.75 mL, 1.675 mmol) and 10% Pd-C (0.6 g). The mixture was stirred under $H_2$ (1 atm) at room temperature overnight. The catalyst was filtered and the solvent was removed. The residue was purified by Sephadex LH-20 column chromatography, eluting with 15% MeOH/toluene, to generate 560 mg (86%) of [A] as a colorless solid: NMR ($CD_3OD$) δ 1.30–1.97 (m, 14H), 2.17 (s, 3H), 2.60 (t, 4H, J=6), 3.00 (t, 2H, J=6), 3.70 (t, 6H, J=6). Anal. ($C_{17}H_{35}ClN_4O_6$) C, H, N.

6,12,18-Tris(benzyloxy)-7,13,19-trioxo-6,12,18-triazaoctacosanenitrile (10)

Compound (8) (1.20 g, 1.95 mmol) was reacted with decanoyl chloride (0.565 g, 2.96 mmol) in $CH_2Cl_2$ and 1N NaOH following the procedure used for (3). Purification by silica gel column chromatography with 2:1 EtOAc/hexane as the eluant provided 1.20 g (80%) of (10) as an oil: NMR δ 0.90 (t, 3H, J=6), 1.13–1.40 (m, 14H), 1.47–1.90 (m, 12H), 2.23–2.53 (m, 8H), 3.50–3.77 (m, 6H), 4.77 (s, 6H), 7.33 (s, 15H). Anal. ($C_{46}H_{64}N_4O_6$) C, H, N.

6,12,18-Trihydroxy-7,13,19-trioxo-6,12,18-triazaoctacosanamine hydrochloride (5)

Compound (10) (1.13 g, 1.47 mmol) was hydrogenated in $CH_3OH$ (150 mL) and 0.1N HCl (16.2 mL, 1.62 mmol) with 10% Pd-C (0.6 g) by the procedure used for [A]. Purification by Sephadex LH-20 column chromatography with 20% EtOH/toluene as the eluant produced 0.508 g (64%) of [A] as a colorless solid: NMR ($CD_3OD$) δ 0.90 (t, 3H, J=6), 1.17–1.87 (m, 28H), 2.33–2.63 (m, 6H), 2.92 (t, 2H, J=6), 3.60 (t, 6H, J=6). Anal. ($C_{25}H_{51}ClN_4O_6$) C, H, N.

14-Bromo-6-(benzyloxy)-7-oxo-6-azatetradecanenitrile [I]

Compound 2 (n=4) (3.2 g, 15.7 mmol) was treated with 8-bromooctanoyl chloride (4.55 g, 18.8 mmol) in $CH_2Cl_2$ and 1N NaOH following the procedure used for (3). Silica gel column chromatography with 2:1 hexane/EtOAc afforded 3.8 g (59%) of [I] as an oil: NMR δ 1.17–2.00 (m, 14H), 2.23–2.50 (m, 4H), 3.37 (t, 2H, J=6), 3.63 (t, 2H, J=6), 4.77 (s, 2H), 7.33 (s, 5H). Anal. ($C_{20}H_{29}BrN_2O_2$) C, H, N.

15-(tert-Butoxycarbonyl)-6,15-bis(benzyloxy)-7-oxo-6,15-diazapentadecanenitrile [II]

N-(tert-Butoxycarbonyl)-O-benzylhydroxylamine (0.991 g, 4.44 mmol) was alkylated with [I] (2.0 g, 4.89 mmol) by employment of the procedure used for (4). Purification of the crude oil by silica gel column chromatography with 3:2 hexane/EtOAc gave 1.98 g (81%) of [II] as an oil: NMR δ 1.13–1.90 (m, 14H), 1.50 (s, 9H), 2.23–2.47 (m, 4H), 3.37 (t, 2H, J=6), 3.63 (t, 2H, J=6), 4.75 (s, 2H), 4.77 (s, 2H), 7.33 (s, 10H). Anal. ($C_{32}H_{45}N_3O_5$) C, H, N.

6,15-Bis(benzyloxy)-7-oxo-6,15-diazapentadecanenitrile [III]

Excess TFA was added to [II] (2.00 g, 3.63 mmol) in $CH_2Cl_2$ at 0° C. The solution was stirred at 0° C. for 30 minutes and at room temperature for 15 minutes, and then the reaction was worked up by the method used for (5). Silica gel column chromatography with 2% MeOH/$CHCl_3$ provided 1.51 g (92%) of [III] as an oil: NMR δ 1.17–1.90 (m, 14H), 2.23–2.50 (m, 4H), 2.90 (t, 2H, J=6), 3.40 (s, 1H), 3.63 (t, 2H, J=6), 4.67 (s, 2H), 4.77 (s, 2H), 7.30 (s, 5H), 7.33 (s, 5H). Anal. ($C_{27}H_{37}N_3O_3$) C, H, N.

23-Bromo-6,15-bis(benzyloxy)-7,16-dioxo-6,15-diazatricosanenitrile [IV]

Compound [III] (1.50 g, 3.32 mmol) was combined with 8-bromooctanoyl chloride (0.963 g, 3.99 mmol) following the conditions used for (3). The crude oil was purified by silica gel column chromatography with 1:1 hexane/EtOAc as the eluant, giving 2.06 g (95%) of [IV] as an oil: NMR δ 1.17–2.00 (m, 24H), 2.23–2.50 (m, 6H), 3.36 (t, 2H, J=6), 3.60 (t, 2H, J=6), 3.63 (t, 2H, J=6), 4.77 (s, 4H), 7.33 (s, 10H). Anal. ($C_{35}H_{50}BrN_3O_4$) C, H, N.

24-(tert-Butoxycarbonyl)-6,15,24-tris(benzyloxy)-7,16-dioxo-6,15,24-triazatetracosanenitrile [IV]

N-(tert-Butoxycarbonyl)-O-benzylhydroxylamine (0.445 g, 1.99 mmol) was alkylated by [IV] (1.37 g, 2.09 mmol), utilizing the procedure followed by (4). Silica gel column chromatography with 1:1 hexane/EtOAc gave 1.50 g (94%) of [V] as an oil: NMR δ 1.50 (s, 9H), 1.17–1.90 (m, 24H), 2.27–2.50 (m, 6H), 3.40 (t, 2H, J=6), 3.60 (t, 2H, J=6), 3.63 (t, 2H, J=6), 4.77 (s 4H), 4.80 (s, 2H), 7.33 (s, 15H). Anal ($C_{47}H_{66}N_4O_7$) C, H, N.

6,15,24-Tris(benzyloxy)-7,16-dioxo-6,15,24-triazatetracosanenitrile [VI]

Excess TFA was added to a solution of [V] (1.32 g, 1.65 mmol) in $CH_2Cl_2$ at 0° C. following the procedure used for (5). The crude oil was purified by silica gel column chromatography using 3:2 EtOAc/hexane to generate 0.9 6 g (83%) of [VI] as an oil: NMR δ 1.17–1.97 (m, 24H), 2.23–2.50 (m, 6H), 2.90 (t, 2H, J=6), 3.57 (t, 2H, J=6), 3.63 (t, 2H, J=6), 4.67 (s, 2H), 4.77 (s, 4H), 7.30 (s, 5H), 7.33 (s, 10H). Anal. ($C_{42}H_{58}N_4O_5$) C, H, N.

6,15,24-Tris(benzyloxy)-7,16,25-trioxo-6,15,24-triazahexacosanenitrile [VII]

Compound [VI] (0.93 g, 1.33 mmol) was treated with acetyl chloride (0.160 g, 2.04 mmol) by the procedure used for (3). Silica gel column chromatography (3:1 EtOAc/hexane) produced 0.95 g (96%) of [VII] as an oil: NMR δ 1.17–1.87 (m, 24H), 2.07 (s, 3H), 2.27–2.47 (m, 6H), 3.47–3.73 (m, 6H), 4.77 (s, 6H), 7.33 (s, 15H). Anal. ($C_{44}H_{60}N_4O_6$) C, H, N.

6,15,24-Trihydroxy-7,16,25-trioxo-6,15,24-triazahexacosanamine hydrochloride [A]

Compound [VII] (1.20 g, 1.62 mmol) was hydrogenated in $CH_3OH$ and 0.1N HCl with 10% Pd-C by the procedure used for [A]. Purification by Sephadex LH-20 column chromatography with 15% EtOH/toluene as the eluant produced 0.386 g (47%) of [A] as a colorless solid: NMR ($CO_3OD$) δ 1.17–1.87 (m, 26H), 2.07 (s, 3H), 2.30–2.55 (m, 4H), 2.90 (t, 2H, J=6), 3.43–3.70 (m, 6H). Anal. ($C_{23}H_{47}ClN_4O_6$) C, H, N.

Biological Evaluation

DFO and the other ligands were administered subcutaneously to fasted rats at 150 μmol/kg in 40% Cremophor RH-40.

Chelator-induced Iron Clearance in Rodents

BILE DUCT CANNULATION

Male Sprague-Dawley rats averaging 400 grams were housed in Nalgene plastic metabolic cages during the experimental period and were given free access to water. The animals were anesthetized using sodium pentobarbital (50 mg/kg) given intraperitoneally (i.p.). The bile duct was cannulated using 22-gauge polyethylene tubing (Intramedic) about 1 cm from the duodenum. The cannula was inserted about 2 cm into the duct and once bile flow was established, the cannula was tied snugly in place. A skin tunneling needle was inserted from the shoulder area around to the abdominal incision. The cannula was threaded through the needle until it emerged from the shoulder opening.

The cannula was passed from the rat to the swivel inside a metal torque-transmitting tether which was attached to a rodent jacket around the animal's chest. The cannula was directed from the rat to a Gilson micro fraction collector by a fluid swivel mounted above the metabolic cage. This system allowed the animal to move freely in the cage while continuous bile samples were being collected. Urine samples were taken every 24 hours.

The efficiency of the C-5, C-8 and C-5/C-10 analogs were compared with subcutaneously administered DFO as a positive control. The efficiencies of the drugs were calculated based on the assumption that DFO and the amideless ligands form a 1/1 complex with iron. These calculations showed the efficiency of DFO to be 2.8±0.7% (range 2.1–4.1%) when the drug was given subcutaneously. Approximately 75% of the ligand-promoted iron excretion was found in the bile and 25% in the urine. When the C-5 compound was administered subcutaneously at the same dose, it was found to be as efficient as DFO, 3.2±0.7% (range 2.7–3.7%). As this compound is more lipophilic, it is not surprising that a larger portion of the iron was excreted in the bile than was seen with DFO, 90% vs. 75%. The C-8 compound with an efficiency of 2.1± 0.4% (range 1.9–2.7%) was approximately 0.75 times as effective as either DFO or the C-5 analog. Again, approximately 90% of the iron excretion was found in the bile. Finally, the efficiency of the C-5/C-10 ligand was found to be only 0.45 times as efficient as DFO, 1.3±0.2% (range 1.1–1.5%). In this case, 94% of the induced iron was excreted in the bile.

I claim:

1. A compound of the formula:

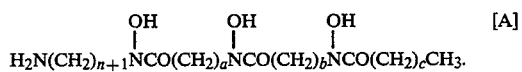

2. A compound according to claim 1 of the formula:

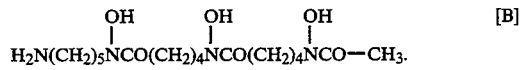

3. A compound according to claim 1 of the formula:

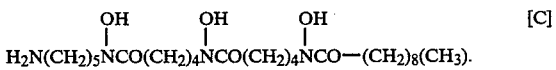

4. A compound according to claim 1 of the formula:

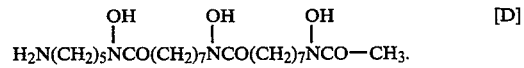

* * * * *

UNITED STATES PATENT AND TRADEMARK OFFICE
CERTIFICATE OF CORRECTION

PATENT NO. : 5,364,965
DATED : November 15, 1994
INVENTOR(S) : Raymond J. BERGERON It is certified that error appears in the above-identified patent and that said Letters Patent is hereby corrected as shown below:

Column 10, line 44 (claim 1, following formula [A]): remove the period and insert the following:

-- wherein: $\underline{n}$ is an integer from 1 to 10; $\underline{a}$ and $\underline{b}$ may be the same or different and are integers from 1 to 10; and $\underline{c}$ may be an integer from 0 to 10. --

Signed and Sealed this

Twenty-first Day of February, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,364,965
DATED : November 15, 1994
INVENTOR(S) : Raymond J. BERGERON, Jr.

It is certified that error appears in the above-identified patent and that said Letters Patent is hereby corrected as shown below:

Column 1, line 15: after "Grant No. 5R01-HL-42817." insert -- The United States Government has certain rights in and to the invention claimed herein. --

Signed and Sealed this

Fourteenth Day of May, 1996

Attest:

BRUCE LEHMAN

*Attesting Officer*   *Commissioner of Patents and Trademarks*